(12) United States Patent
Crowley et al.

(10) Patent No.: US 7,671,586 B2
(45) Date of Patent: Mar. 2, 2010

(54) APPARATUS AND METHOD FOR NON-SYMMETRIC MAGNETIC FIELD BALANCING IN AN INSPECTION SCANNER

(75) Inventors: Christopher Crowley, San Diego, CA (US); Michael Urbach, Poway, CA (US); Oscar Mitchell, San Diego, CA (US); Kevin Derby, Carlsbad, CA (US); Adam Drew, Oceanside, CA (US)

(73) Assignee: Morpho Detection, Inc., Newark, CA (US)

( * ) Notice: Subject to any disclaimer, the term of this patent is extended or adjusted under 35 U.S.C. 154(b) by 0 days.

(21) Appl. No.: 11/955,014

(22) Filed: Dec. 12, 2007

(65) Prior Publication Data

US 2009/0001975 A1 Jan. 1, 2009

Related U.S. Application Data

(63) Continuation of application No. 11/559,725, filed on Nov. 14, 2006, now Pat. No. 7,327,137.

(51) Int. Cl.
*G01V 3/00* (2006.01)
(52) U.S. Cl. .................... 324/300; 324/309
(58) Field of Classification Search ......... 324/300–322; 600/407–443
See application file for complete search history.

(56) References Cited

U.S. PATENT DOCUMENTS

| 6,853,194 | B2* | 2/2005 | Nelson et al. ............... 324/329 |
| 7,227,466 | B2* | 6/2007 | Nelson ....................... 340/551 |
| 7,327,137 | B1* | 2/2008 | Crowley et al. ............. 324/300 |
| 7,352,180 | B2* | 4/2008 | Manneschi .................. 324/307 |
| 7,365,536 | B2* | 4/2008 | Crowley et al. ............. 324/300 |
| 7,514,924 | B2* | 4/2009 | Luedeke et al. ............. 324/309 |
| 2005/0073307 | A1* | 4/2005 | Manneschi .................. 324/316 |
| 2005/0247472 | A1* | 11/2005 | Helfer et al. .................. 174/36 |
| 2006/0255798 | A1* | 11/2006 | Crowley et al. ............. 324/300 |
| 2007/0211922 | A1* | 9/2007 | Crowley et al. ............. 382/115 |
| 2008/0315874 | A1* | 12/2008 | Crowley ..................... 324/307 |

* cited by examiner

*Primary Examiner*—Brij B Shrivastav
(74) *Attorney, Agent, or Firm*—Armstrong Teasdale LLP

(57) ABSTRACT

An inspection system positions a balancing shim to asymmetrically balance a magnetic field generated by an inductive sensor, which forms part of the inspection system. Additionally, relays and capacitors used to tune the inductive sensor to a desired resonance frequency are geometrically arranged to minimize electrical interference generated by operation of the relays and capacitors. A shielding device, which may be formed on a printed circuit board, protects a magnetic field generated by the inductive sensor from external electromagnetic interference. A slot positioned in the inductive sensor may be used to tune a resonant mode of the inductive sensor to accurately and particularly detect metallic shanks and/or other metallic objects in shoes, socks, and/or clothing.

19 Claims, 10 Drawing Sheets

APPARATUS AND METHOD FOR NON-SYMMETRIC MAGNETIC FIELD BALANCING IN AN INSPECTION SCANNER

CROSS REFERENCE TO RELATED APPLICATIONS

This application is a continuation of U.S. patent application Ser. No. 11/559,725, filed 14 Nov. 2006 now U.S. Pat. No 7,327,137.

BACKGROUND OF THE INVENTION

1. Field of the Invention

The field of the invention relates to security inspection systems generally, and more particularly, to a security inspection system having: an apparatus configured to asymmetrically balance a magnetic field generated by an inductive sensor; an apparatus configured to minimize vulnerability to electromagnetic interference caused by random geometrical arrangements of relays and capacitors used to operate the inductive sensor; an apparatus configured to protect magnetic fields generated by the inductive sensor from external electrical interference; and an apparatus for detecting shanks in shoes worn by an inspected person.

2. Discussion of Related Art

Extant security inspection systems use known technologies such as nuclear magnetic resonance (NMR), nuclear quadrupolar resonance (NQR), metal detection, and x-rays, among others, to detect weapons, explosives, illegal drugs, and other kinds of substances of interest in and/or on an item, such as shoes, luggage, clothing, and the like.

When security is heightened, persons to be scanned are often required to remove their shoes. The shoes are then typically placed in plastic tubs that move, via a conveyor belt, into an x-ray scanner. Additionally, or alternatively, security personnel may visually inspect the shoes, swab the interior and/or exterior of the shoes for trace detection purposes, and/or pass a hand-held metal detector over the shoes. Such methods consume time, inconvenience passengers, and slow the rate of a security checkpoint's throughput. A need therefore exists for a solution that enables simple and accurate detection of weapons, explosives, drugs, and/or other substances of interest that may be hidden in a person's shoes while the shoes are being worn. Another need exists for a solution that provides simple and accurate detection of weapons, explosives, illegal drugs, and/or other substances of interest that may be hidden, alternatively or additionally, in the person's socks and/or clothing present on the person's lower extremities while such socks and/or clothing are being worn.

Various devices have been developed in attempts to provide solutions to one or more of these needs. One example of such a device is a walkthrough NQR shoe scanner that positions a NQR sensor in the floor of the shoe scanner and flanks the NQR sensor with two opposing vertical side walls that are electrically connected to the floor of the shoe scanner. A channel formed by the space between the opposing vertical side walls extends the length of the shoe scanner so that a person can enter one (open) end of the shoe scanner and exit the opposite (open) end. As the person stands in the central portion of the NQR shoe scanner, the NQR sensor operates to detect alarm objects (e.g., weapons, explosives, illegal drugs, etc.) in or on the person's shoes, socks, or articles of clothing.

Another example is a passenger screening system that positions an inductive NQR sensor in a floor of the passenger screening system and flanks the inductive NQR sensor with three vertical, electrically conductive walls that are joined together and attached to the floor of the passenger screening system. The three vertical, electrically conductive walls include two electrically conductive and opposing side walls and one electrically conductive end wall. A channel formed by the space between the opposing side walls extends from an open end of the passenger screening system to the end wall that forms the opposite end of the passenger screening system so that a person can enter and exit the passenger screening system only from the open end of the channel. The passenger screening system also includes a metal detection sensor having two metal detector conductive traces—a first metal detector conductive trace positioned on one of the opposing side walls; and a second metal detector conductive trace positioned on the other of the opposing side walls. The metal detector conductive traces are configured to generate a uniform magnetic field when no metallic object or substance is present within the scanning area. Any metallic object or substance that is later positioned within the scanning area will disturb the otherwise balanced magnetic field generated by the metal detection conductive traces. This disturbance creates an electrical and/or magnetic imbalance between the metal detector conductive traces, which causes the passenger screening system to receive a signal indicating that a metallic object has been detected within the scanning area.

Known security inspection systems, such as the walk-through NQR shoe scanner and the passenger screening system, illustratively described above, have several disadvantages. Principal among them is that the magnetic field becomes imbalanced when the channel is capped by a kiosk and/or an end wall. Additionally, the magnetic field degrades if not effectively shielded from at least the electric component of internal and/or external electromagnetic fields. Thus, in addition to these needs referenced above, a need exists for a shoe scanner that asymmetrically balances a magnetic field generated by an inductive sensor. A need also exists for a shoe scanner that shields the magnetic field from vulnerability to electromagnetic interference caused by random geometrical arrangements of relays and capacitors used to operate the inductive sensor. An additional need exists for an asymmetric, electrically shielded shoe scanner configured to simply and accurately detect the presence of a metallic shoe shank in shoes worn by an inspected person.

BRIEF DESCRIPTION OF THE INVENTION

The technology disclosed herein overcomes the disadvantages associated with the related art and meets the needs discussed above by providing an inspection system that, among other advantages and technical effects: positions a balancing shim to asymmetrically balance a magnetic field generated by an inductive sensor; symmetrically positions geometric arrangements of switches and relays used to operate the inductive sensor to minimize electrical interference; provides a shielding device that protects a magnetic field generated by the inductive shoe sensor from internal and external electrical interference; and positions a slot in an inductive sensor to tune a resonant mode of the inductive sensor to accurately and particularly detect metallic shanks in shoes.

In an embodiment, an inspection system comprises an electromagnetic shield. The electromagnetic shield includes two opposing side walls, an end wall electrically connected to each of the two opposing side walls, and a floor. The floor includes a recessed housing and is electrically connected to each of the two opposing side walls and to the end wall. The two opposing side walls, the end wall, the floor, and the recessed housing are each formed of an electrically conductive material. The inspection system further comprises an inductive sensor positioned within the electromagnetic shield. The inductive sensor comprises at least two conductive traces positioned on opposing sides of a medial plane of the electromagnetic shield. The inspection system also comprises means for balancing a magnetic field, the means for balancing a magnetic field being positioned between, and electrically insulated from, the at least two conductive traces.

In an embodiment, an inspection system comprises an electromagnetic shield. The electromagnetic shield comprises two opposing side walls, an end wall electrically connected to each of the two opposing side walls, a floor including a recessed housing and electrically connected to each of the two opposing side walls and the end wall. The two opposing side walls, the end wall, the floor, and the recessed housing are each formed of an electrically conductive material. The inspection system further comprises an inductive sensor positioned in a space defined by the electromagnetic shield. The inductive sensor comprises at least two conductive traces positioned on opposing sides of a medial plane of the electromagnetic shield. The inspection system further comprises a shielding device positioned within the electromagnetic shield and configured to protect a magnetic field associated with each of the at least two conductive traces from external electromagnetic interference.

In an embodiment, an inspection system comprises an electromagnetic shield. The electromagnetic shield comprises two opposing side walls, an end wall electrically connected to each of the two opposing side walls, a floor including a recessed housing and electrically connected to each of the two opposing side walls and the end wall. The two opposing side walls, the end wall, the floor, and the recessed housing are each formed of an electrically conductive material. The inspection system further comprises an inductive sensor positioned in a space defined by the electromagnetic shield. The inductive sensor comprises at least two conductive traces positioned on opposing sides of a medial plane of the electromagnetic shield. The inspection system further comprises a symmetrically balanced geometrical arrangement of relays and capacitors used to operate the inductive sensor.

An embodiment of the invention includes a method. The method comprises a step of detecting a presence of an item within a scanning area of an inspection scanner that includes means for asymmetrically balancing a magnetic field. The method further comprises a step of exciting one or more conductive traces with electromagnetic signals at a pre-determined resonance frequency that corresponds to a characteristic resonance frequency of a pre-determined alarm object. The method further comprises generating the magnetic field in response to the electromagnetic signals. The method may further comprise asymmetrically balancing the magnetic field to improve performance of the shoe scanner.

BRIEF DESCRIPTION OF THE DRAWINGS

The above and other aspects of various embodiments of the claimed invention will become more apparent when the following detailed description is considered together with the accompanying drawings in which:

DETAILED DESCRIPTION OF THE INVENTION

Figure 1:
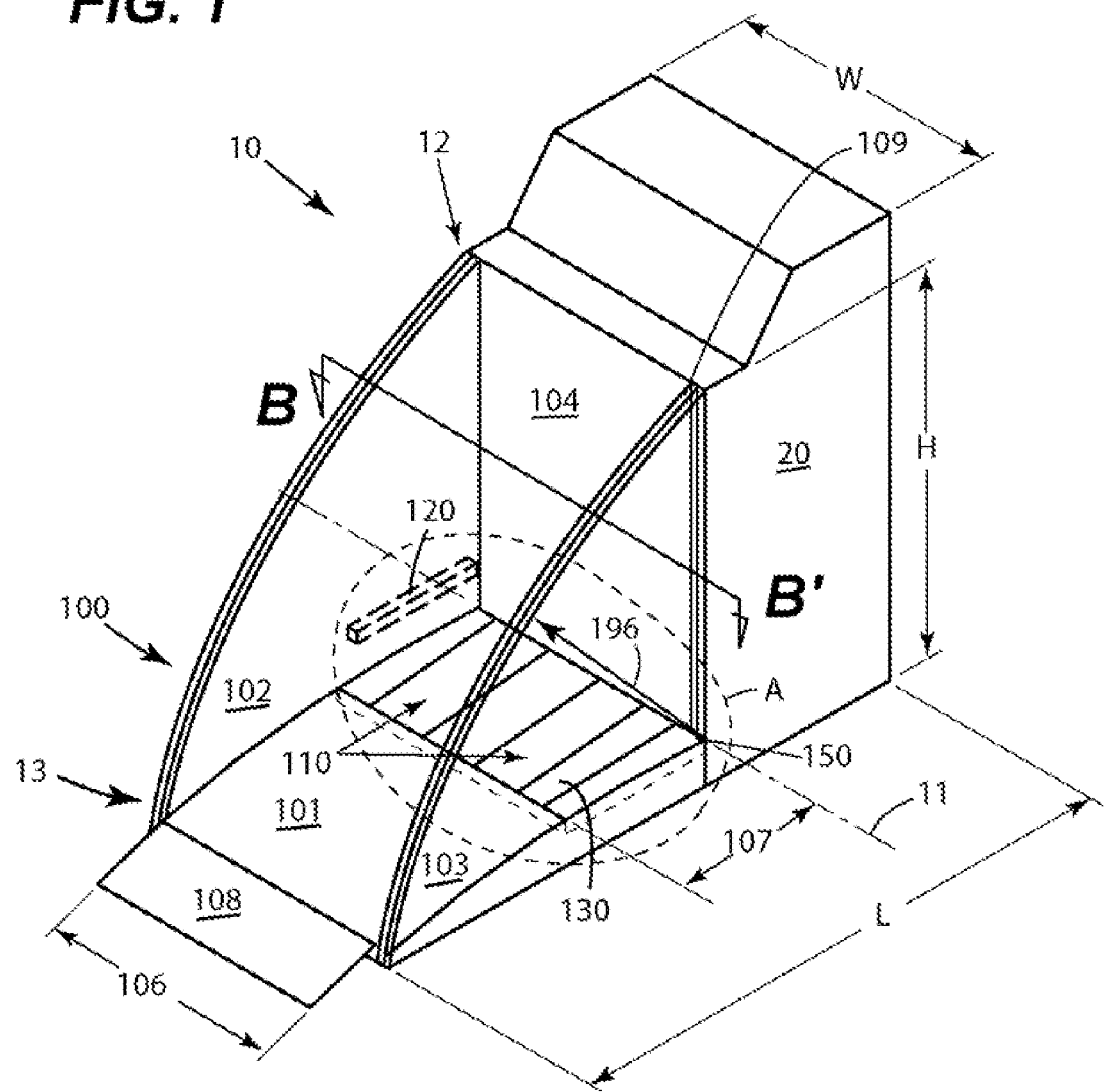
FIG. 1 is a frontal perspective, cut-away view of an embodiment of an inspection system that includes an identification kiosk integrated with an asymmetric shoe scanner.

Reference is made herein to the accompanying drawings briefly described above, which show by way of illustration various embodiments of the claimed invention. Persons of ordinary skill in the above-referenced technological field will recognize that other embodiments may be utilized, and that structural, electrical, and procedural changes may be made without departing from the scope of the claimed invention. As used herein, the singular (illustratively, "shoe") includes the plural (illustratively, "shoes"), and the plural includes the singular. As used herein, the term "shoe" comprises any type of natural or man-made article that can be worn on the entirety or a portion of a human leg. As used herein, the term "kiosk" comprises an area or structure, open on one or more sides, that is configured for one or more special uses that are described herein. Non-limiting examples of such special uses include identity card identification and/or biometric identification of a registered traveler, trace detection analysis of particles and/or substances derived from a person, etc.

As a matter of convenience, many embodiments of the invention are described in the context of a walk-up identification kiosk implemented as part of a typical aviation security system. Accordingly, particular reference may be made to a "person," "shoes," "socks," and "articles of clothing," and the like, that are screened for alarm object(s) (e.g., weapons, explosives, illegal drugs, and other substances of interest); however, embodiments of the present invention are not limited to applications in the aviation security field. Rather, many other applications are envisioned and possible within the teachings of this disclosure. For example, embodiments of an asymmetric shoe scanner integrated with a walk-up identification kiosk inspection system may also be implemented at seaports, sports stadiums, racetracks, public buildings, public transportation facilities, prisons, hospitals, power plants, court houses, office buildings, hotels, and casinos, among others.

An embodiment of a passenger inspection system having an asymmetric nuclear quadrupole resonance (NQR) or nuclear magnetic resonance (NMR) shoe scanner, a metal detection sensor, and/or an identification kiosk may be used to implement the Registered Traveler program sponsored by the U.S. Transportation Security Administration (TSA). This program is designed to provide expedited security screening for passengers who volunteer biometric and biographic information to a TSA-approved vendor and who successfully complete an initial security threat assessment.

For example, rather than standing in slow-moving security lines, registered travelers may bypass such security lines and walk into an embodiment of a passenger inspection system constructed in accordance with the principles of the invention. Once positioned within an embodiment of the inspection system, the registered travelers may have their ID card information and/or biometric information validated by an identification kiosk that forms part of the inspection system. At about the same time, the registered travelers may be scanned by the inspection system's metal detection sensor for the presence of metallic objects such as shoe shanks. Additionally, the registered travelers may be screened by the inspection system's inductive NQR/NMR sensor for the presence of alarm objects, that are in, on, and/or proximate their shoes. If a metallic object (e.g., a shoe shank, a weapon, an explosives container, an explosives ignition device, etc.) or another type of alarm object (e.g., an explosive chemical, an illegal drug, and/or other substances of interest) is detected, the registered traveler may be asked to undergo additional security inspection and/or screening. Additionally, if only a metallic object is detected, the registered traveler may be informed that the current additional inspection and/or screening may be avoided on future trips by wearing shoes and/or clothing that do not contain metallic objects. If the registered traveler's identity is properly verified, and no metallic objects or other types of alarm objects are otherwise detected, the registered traveler may be permitted to quickly pass through (or bypass) one or more security checkpoints that are required for all non-registered travelers.

Embodiments of the invention are now described with respect to FIGS. 1, 2, 3, 4, 5, 6, 7, 8, 9, 10, 11, and 12. With respect to FIG. 1, the term "fore" refers to a closed end 12 of a shoe scanner 100 that is proximate an identification kiosk 20; and the term "aft" refers to an opposite open end 13 of the shoe scanner 100. Additionally, in FIG. 2 and following, the term "fore" refers to portions of the inspection system 10 that are "above" a lateral center axis 123; and the term "aft" refers to portions of the inspection system 10 that are "below" the lateral center axis 123. As used herein, the term "asymmetric shoe scanner" refers to an embodiment of a shoe scanner 100 that is not symmetric about a system center axis 11, which is defined as the midpoint of a length "L" of the inspection system 10. The length "L" of the inspection system 10 may be a distance measured from an outer edge of the channel 106 to an outer edge of the identification kiosk 20, as illustratively shown in FIG. 1. The inspection system 10 further includes a width "W" and a height "H," each of which is further defined below.

FIG. 1 is a frontal perspective, cut-away view of an embodiment of an inspection system 10 that includes an identification kiosk 20 integrated with an asymmetric shoe scanner 100. In operation of one embodiment, a person enters the open end 13 of the shoe scanner 100 and stands facing the end wall 104. The fore end of the shoe scanner 100 is bounded by the end wall 104, and the aft end of the shoe scanner 100 is open to permit a person to enter and exit the shoe scanner 100. Such an asymmetric configuration unbalances a magnetic field generated when the shoe scanner 100 operates. Specifically, the magnetic field becomes unbalanced when the end wall 104 reflects a frontal portion of the magnetic field aft toward the open end 13 of the shoe scanner 100. This phenomenon is shown in and further described below with respect to FIG. 6. Such an unbalanced magnetic field is herein called an "asymmetric magnetic field."

Referring again to FIG. 1, an embodiment of the inspection system 10 comprises a passive, open-access electromagnetic shield formed of a floor 101, two vertical opposing side walls 102,103, and an end wall 104. Each of the side walls 102,103 and the end wall 104 are electrically connected with each other and to the floor 101 via welding and/or other known electrically conductive fastening techniques. Together, the electrically connected floor 101, the side walls 102,103, and the end wall 104 function to shield at least an inductive sensor 110 from external EMI/RFI (electromagnetic interference/radio frequency interference) noise. They also inhibit RF energy from escaping the asymmetric shoe scanner 100 during a NQR/NMR inspection processes and/or a metal detection inspection process. To reduce the amount of shielding required, the inductive sensor 110 may be configured to only excite well-attenuated resonant modes.

In an embodiment, the inductive sensor 110 is one of a nuclear quadrupole resonance ("NQR") sensor and a nuclear magnetic resonance ("NMR") sensor. For convenience only, various embodiments are described herein with the inductive sensor 110 implemented as a NQR sensor, but such description is equally applicable to other types of inductive sensors.

In an embodiment a recessed housing 150 may be formed in the floor 101. One or more components of the inductive sensor 110 may be positioned above or in the recessed housing 150. In contrast to conventional walk-through shoe scanners, the end wall 104 prevents a person that enters the open end 13 of the asymmetric shoe scanner 100 from walking out of the asymmetric shoe scanner 100 except back through the open end 13. In an embodiment, the end wall 104 may comprise part of the identification kiosk 20. A channel 106, including a scanning area 107, is formed by the space bounded by the side walls 102 and 103 and the end wall 104. A ramp 108 connected to an end of the floor 101 may be included at the open end 13 of the channel 106.

Each of the floor 101, the side walls 102, 103, and the end wall 104 may be formed of a solid electrically conductive material or of pieces of electrically conductive materials joined to a frame. Examples of suitable electrically conductive materials include, but are not limited to, aluminum and copper. Illustratively, side wall 103 is cut-away to show an embodiment of such a frame 109.

The overall size and shape of the inspection system 10 are chosen to provide the necessary electromagnetic shielding for the type and power of the inductive NQR sensor 110 and/or the magnetic sensor 120 being implemented. Illustratively, the side walls 102,103 and end wall 104 have an overall height "H". This height "H" may be measured as the distance between a top surface of a substrate supporting the inspection system 10 and the highest portion of the walls side walls 102,103, and the end wall 104. The width "W" of the inspection system 10 may be measured as the distance between the side walls 102 and 103. In an embodiment, the height "H" may range from about 71.1 cm to about 106.7 cm, and the width "W" may range from about 61 cm to about 91.4 cm. The embodiment of FIG. 1 shows the left and right walls 102,103 formed with optionally truncated portions at the open end 13 of the channel 106. Truncating the side walls 102,103 in this manner eases movement into and out of the inspection system 10.

The surfaces of the floor 101 and side walls 102,103 that are within an interior of the electromagnetic shield may be formed of (or may be covered and/or coated with) a durable wear-resistant material of a type known to a person of ordinary skill in the art. At least the interior surface of the floor 101 and/or the top surface of the ramp 108 may covered with a skid-resistant material to prevent a person entering or exiting the asymmetric shoe scanner 100 from slipping and/or falling. Optionally, the interior surface of the floor 101, or a durable wear-resistant material covering/coating the floor 101, may be marked to show a person where within the scanning area 107 to stand (or place an item) so that the person (or item) can be scanned by the inductive NQR sensor 110 and/or the magnetic sensor 120 that form part of the asymmetric shoe scanner 100. In this regard, dotted-line silhouettes 116,117 of feet are included in FIG. 2 (further described below) to illustrate approximate areas within the scanning area 107 where a person's feet (or other items) may be placed for scanning by the one or more inductive sensors 110, 120.

Unlike some conventional inspection systems, embodiments of the inspection system 10 of the present invention do not require a person to remove their shoes, socks, or clothing for scanning. Instead, the person may wear the socks, shoes, clothing, and the like directly into the asymmetric shoe scanner 100, and the scanning for alarm objects (e.g., weapons, explosives, illegal drugs, and the like) may occur as the person conducts a transaction at the identification kiosk 20. For example, an appropriately configured inductive NQR sensor 110 can detect a wide range of explosives such as Semtex plastic explosive, C-4 plastic explosive, nitroglycerin, pentaerythritol tetranitrate (PETN), cyclotrimethylenetrinitramine (commonly known as "RDX," "cyclonite," or "hexogen"), DETASHEET™ plastic explosive manufactured by E. I. du Pont de Nemours and Company, trinitrotoluene (TNT), trinitrophenylmethylnitramine (Tetryl), ammonium-nitrate fuel oil (ANFO), black powder, and the like.

In accordance with an embodiment, the inductive sensor 110 may be positioned atop and/or within a recessed housing 150 of the floor 101, between the entrance ramp 108 and the end wall 104. This recessed region within the floor 101 may extend beneath all or part of the scanning area 107. Although the inductive sensor 110 is shown positioned within or atop the recessed housing 150, an alternative is to mount the recessed housing 150 and included inductive sensor 110 onto a substantially flat portion of the walkway between the entrance ramp 108 and the end wall 104. Such a configuration would require an inspected person to step up and onto the recessed housing 150 for inspection. Components of a magnetic sensor 120 may be incorporated into each of the side walls 102 and 103.

Although not shown, an embodiment of the asymmetric shoe scanner 100 may include a radio frequency (RF) subsystem having a variable frequency RF source in communication with the inductive NQR sensor 110 and configured to provide an RF excitation signal to an item positioned with the scanning area 107. Relays and capacitors of the inductive sensor 110 are used to tune the frequency of the RF excitation signal to a desired resonant mode. The resonant mode, and its corresponding RF excitation signal frequency (or range of frequencies), will vary depending on the type of alarm object being detected. In an embodiment, the frequency of the RF excitation signal equals or approximates a predetermined, characteristic nuclear quadrupolar resonance frequency of a pre-determined alarm object. In such an embodiment, the inductive NQR sensor 110 may be configured to function as a pickup coil for NQR signals from the item generated in response to the RF excitation signal, and further configured to provide a NQR output signal indicative of a presence or absence of the substance of interest. Thus, the inductive sensor 110 may provide electrical (and/or magnetic) excitation to an item positioned within the scanning area 107. Alternatively, the inductive sensor 110 may be a nuclear magnetic resonance (NMR) sensor used to provide an excitation signal that equals or approximates a predetermined, characteristic NMR frequency of a predetermined alarm object.

Illustratively, a NQR sensor operates by surrounding an atomic quadrupolar nucleus within an electric field gradient. When an atomic quadrupolar nucleus is within the radio frequency magnetic field, variations in the local field associated with the field gradient affect different parts of the nucleus in different ways. The combined forces of these fields cause the quadrupolar nucleus to experience a torque, which causes it to precess about the electric field gradient. Precessional motion generates an oscillating nuclear magnetic moment. An externally applied radio frequency (RF) magnetic field in phase with the quadrupole's precessional frequency can tip the orientation of the nucleus momentarily. The energy levels are briefly not in equilibrium, and immediately begin to return to equilibrium. As the nuclei return, they produce an RF signal, known as the free induction decay (FID).

The skilled artisan will recognize that the aforementioned excitation of an item may be used to generate a NQR signal from the item. The inductive sensor 110 detects the resulting NQR signal, which is subsequently amplified by a sensitive receiver and processed by a computer processor to measure its characteristics. A computer-generated signal indicative of the presence or absence of the pre-determined alarm object may result from the processing of the free induction decay.

Additionally, the inspection system 10 may further include a computer system for operating and controlling the asymmetric shoe scanner 100 and/or the identification kiosk 20. An embodiment of such a computer system is further described below with respect to FIG. 9.

Figure 2:
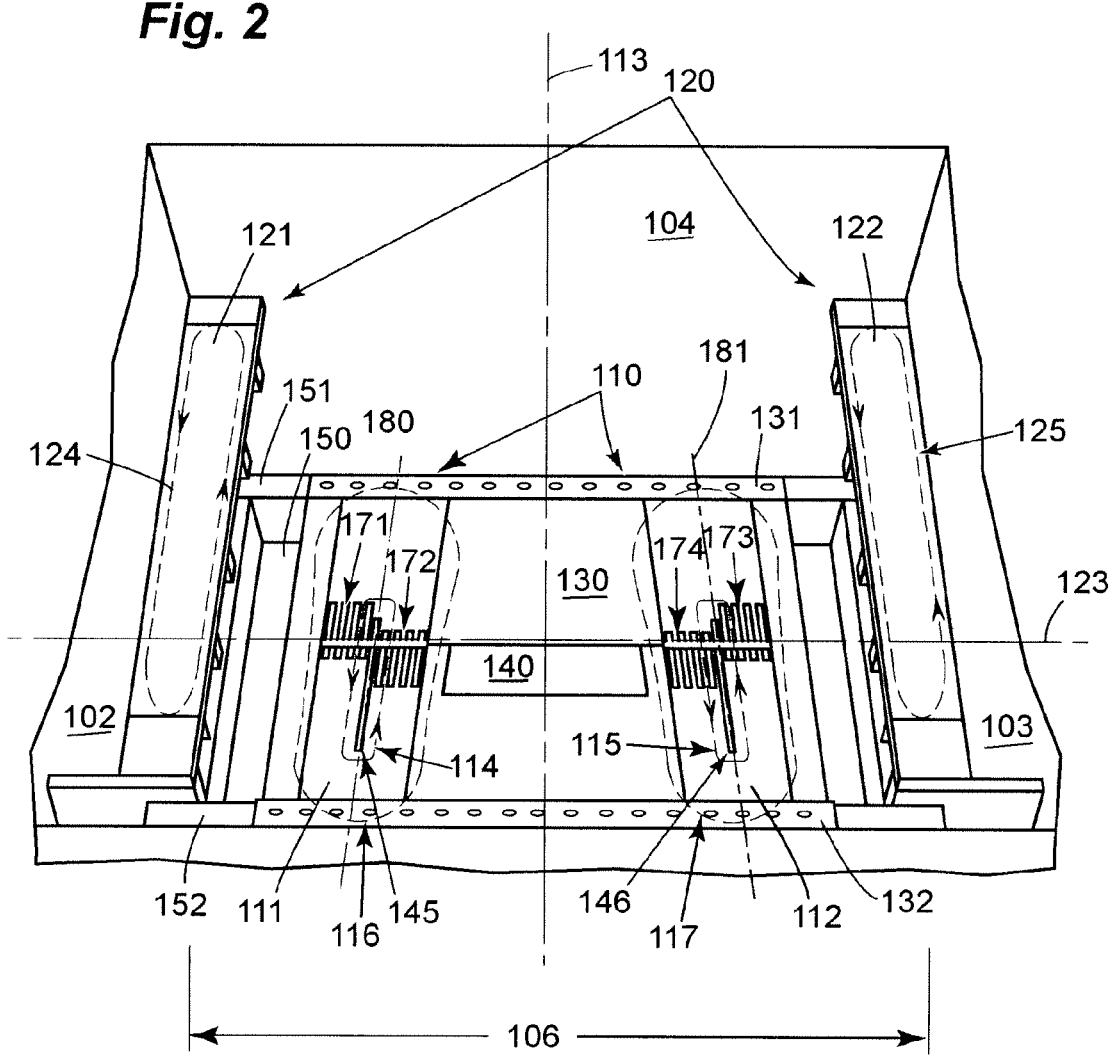
FIG. 2 is a top perspective view of the enlarged area "A" shown in FIG. 1 that further illustrates an exemplary configuration of first, second, third, and fourth conductive traces within an electromagnetic shield having four electrically conductive walls.

FIG. 2 is a top perspective view of the enlarged area "A" of the asymmetric shoe scanner 100 shown in FIG. 1 that further illustrates an exemplary configuration of a first conductive trace 111, a second conductive trace 112, a first metal detector conductive trace 121, and a second metal detector conductive trace 122 within an electromagnetic shield having four electrically conductive walls 101, 102, 103, and 104. For purposes of illustration, the interior durable, skid-resistant surface of the floor 101 has been removed from FIG. 2 to more clearly show the recessed housing 150, and the printed circuit board 130, and the and conductive traces 111,112 that form part of the inductive NQR (or NMR) sensor 110. Also, for purposes of illustration, the interior surfaces of the side walls 102,103 have been removed from FIG. 2 to more clearly show the first metal detector conductive trace 121 and the second metal detector conductive trace 122, which collectively form the magnetic sensor 120 described above.

As shown in FIG. 2, an inductive sensor 110 may be implemented using two conductive traces 111,112. Each of these conductive traces 111,112 may be formed as part of a printed circuit board 130 and located on opposing sides of the medial plane 113 of the printed circuit board 130. The fore edge 131 and aft edge 132 of the printed circuit board 130 may be electrically coupled with fore portion 151 and aft portion 152 of the recessed housing 150. As shown in FIG. 2, the conductive trace 111 is positioned on one side of medial plane 113, while the conductive trace 112 is positioned on the opposite side of the medial plane 113.

In an embodiment, a magnetic field balancing shim 140 is integrated as a component of the asymmetric shoe scanner 100. Without the shim 140, the end wall 104 of the asymmetric shoe scanner 100 unbalances the NQR/NMR magnetic field generated when the asymmetric shoe scanner 100 operates by reflecting a fore portion of the magnetic field back towards the lateral center axis 123. If left uncorrected, the unbalanced magnetic field may introduce errors into the data collected by the asymmetric shoe scanner 100 and/or render the asymmetric shoe scanner 100 inoperable. Accordingly, embodiments of the invention provide the shim 140 (and specially position it) to balance the NQR/NMR magnetic field in a way that allows the asymmetric shoe scanner 100 to operate in an optimal manner with high throughput and a low percentage of false alarms. Note the lateral center axis 123 is different from the system center axis 11 shown in FIG. 1. As mentioned above, the lateral center axis is used herein to define fore and aft symmetry of the inductive NQR sensor 110 and the magnetic sensor 120.

In an embodiment, the shim 140 is formed within the printed circuit board 130. In another embodiment, the shim 140 is affixed to an outer surface of the printed circuit board 130 using an adhesive or a fastener. In either embodiment, the shim 140 may be a generally flat, rectangular piece of material having electrically conductive properties. One example of a suitable material is copper, but other electrically conductive materials, or combinations of materials may also be used. The shim 140 is placed between, and electrically insulated from, the conductive traces 111,112. Additionally, a vertical center axis of the shim 140 is aligned with the medial plane 113. To balance the NQR/NMR magnetic field by deflecting it towards the end wall 104, the fore edge 141 of the shim 140 should be positioned at or slightly aft (e.g., below) of the lateral center axis 123 that extends from a first side wall 102 of the two opposing side walls to a second side wall 103 of the two opposing side walls 102,103.

The dimensions of the shim 140 will vary depending on a number of factors, including, but not limited to: the dimensions of the circuit board 130, the dimensions of the conductive traces 111,112, and the strength of the NQR magnetic field, among others. In the embodiment illustratively shown in FIG. 2, the shim 140 has a width 142 (measured parallel to the lateral center axis 123) greater than its depth 143 (measured parallel to the medial plane 113).

As shown in FIG. 2, and as further described below with respect to FIG. 3, operation of the asymmetric shoe scanner 100 creates different current loops in one or more of the printed circuit board 130, the conductive traces 111,112 of the inductive NQR sensor 110, and the conductive traces 121,122 of the magnetic sensor 120. The details and direction of the largest current loop, which is formed in the printed circuit board 130 and the conductive traces 111,112, are described below with reference to FIG. 3. Smaller, self-contained current loops 124,125 are respectively formed in each of the metal detector conductive traces 121,122 of the magnetic sensor 120. Two additional self-contained slot current loops 114,115 may be respectively formed in each of the conductive traces 111,112.

If shoe shank detection slots 145,146 are respectively formed in the conductive traces 111,112, they may be configured in such a manner that the conductive trace 111 experiences a current flow that is generally or substantially parallel to the side wall 102, and in such a manner that the conductive trace 112 experiences a separate current flow that is generally or substantially parallel to the side wall 103. To achieve these current flows, the conductive traces 111,112 may be placed in communication with an electrical source (not shown in this figure), such as the RF excitation source described above. It is understood that the current loops 124,125 and the slot current loops 114,115 are drawn merely for illustration and would not appear in an embodiment of the manufactured apparatus.

Referring again to FIG. 2, a magnetic sensor 120 may be constructed using at least two conductive traces 121,122 that are electrically insulated the printed circuit board 130. The first metal detector conductive trace 121 may be attached to the side wall 102, and the second metal detector conductive trace 122 may be attached to the side wall 103. As shown, the first metal detector conductive trace 121 is located on one side of the medial plane 113 of the channel 106, and the second metal detector conductive trace 122 is located on the opposite side of the medial plane 113.

The magnetic sensor 120 may be configured in such a manner that the first metal detector conductive trace 121 experiences a current flow that is generally or substantially parallel to the side wall 102, and in such a manner that the second metal detector conductive trace 122 experiences a separate current flow that is generally or substantially parallel to the side wall 103. To achieve these current flows, the first and second metal detector conductive traces 121,122 may be placed in communication with an electrical source (not shown).

In an embodiment, the magnetic sensor 120 may be configured to detect metallic objects in a number of different orientations that are present within the vicinity of the lower extremities of an inspected person. In such an embodiment, the inspection system 10 may utilize the inductive sensor 110 to additionally or alternatively detect a metallic object, such as a gun, a knife, a razor, and other bladed weapons, present near the lower extremities of the inspected person.

In a particular embodiment shown in FIG. 2, the inductive sensor 110 is configured to detect a shift in a tune frequency resulting from a presence of a shank located in a shoe or shoes of an inspected person. Thus, each of the conductive traces 111,112 is provided with means for generating a resonant mode to detect a presence of a shank within a shoe. In one embodiment, this means for generating a resonant mode comprises vertical slots 145,146 in each of the conductive traces 111 and 112, respectively. Each of the vertical slots 145,146 may be formed in and generally centered over the respective longitudinal axes 180,181 that extend through the centers of each of the conductive traces (e.g., coils) 111,112, respectively. A majority of a length of the slot 145 may be positioned in the aft part of the conductive trace 111 (e.g. in the fore end of the aft conductive element 162 of conductive trace 111). Similarly, a majority of a length of the slot 146 may be positioned in the aft end of the conductive trace 112) (e.g. in the fore end of the aft conductive element 164 of conductive trace 112). The slots 145,146 each function to produce a new resonant mode (e.g., the presence of each of the slots 145,146 creates a range of resonance frequencies particularly suited to detecting a presence of metallic shanks within one or more shoes placed within the scanning area 107).

As described below, when the unique resonant mode(s) (or range of resonant modes) provided by the shoe shank detection slots 145,146 is excited, the inductive sensor 110 acts as a shoe shank detector that detects a change or shift in the resonance tune frequency resulting from the presence of a metallic shank located in the shoe or shoes of an inspected person.

For example, in an embodiment, each of the metal detector conductive traces 121,122 may be driven by a generator (not shown) to create a magnetic field, which creates resonant slot currents 114,115, respectively in the conductive traces 111, 112 of the inductive sensor 110. The magnetic field is generally uniform if no metallic objects or substances are present; however a metallic object or substance positioned over either (or both) of shoe shank detection slots 145, 146 will alter the magnetic field (and its resulting resonant slot currents 114, 115). Thus, a change in the resonant slot currents 114,115 can indicate the presence of a metallic shoe shank (and/or other metallic object and/or substance).

The inductive sensor 110 may be coupled with a computer processor. Accordingly, the shift in a resonant tune frequency associated with a shoe shank resonant mode may be correlated by the computer system 300 (of FIG. 9) to the presence of a metallic shank concealed within the inspected person's shoe. If a shank is detected, the computer system 300 may output a signal to the identification kiosk graphical user interface that informs the inspected person they will require further scanning at another security checkpoint. In one embodiment where the inspection system 10 is implemented at a ticketing area of an airport, this second security checkpoint may be a gate area checkpoint. If no metallic objects or substances are detected, the person may be allowed to quickly pass through (or bypass) one or more security checkpoints.

In FIGS. 1 and 2, the inspection system 10 is shown having an open-access entrance, which is defined by the substantially U-shaped design of this structure. If desired, the inspection system 10 may alternatively be configured with gates, doors, or other enclosure devices. Although the inspection system 10 is fully functional without being configured as a fully-enclosed shielded enclosure, such a design is possible. Note further that NQR/NMR/metal detection sensors 110,120 in accordance with various embodiments of the present invention not only provide screening for explosives, illegal drugs, and metallic objects, for example, as part of a inspection system 10, but such sensors may be implemented to cooperate with other types of inspection systems as well (for example, vapor trace, x-ray, and the like).

Figure 3:
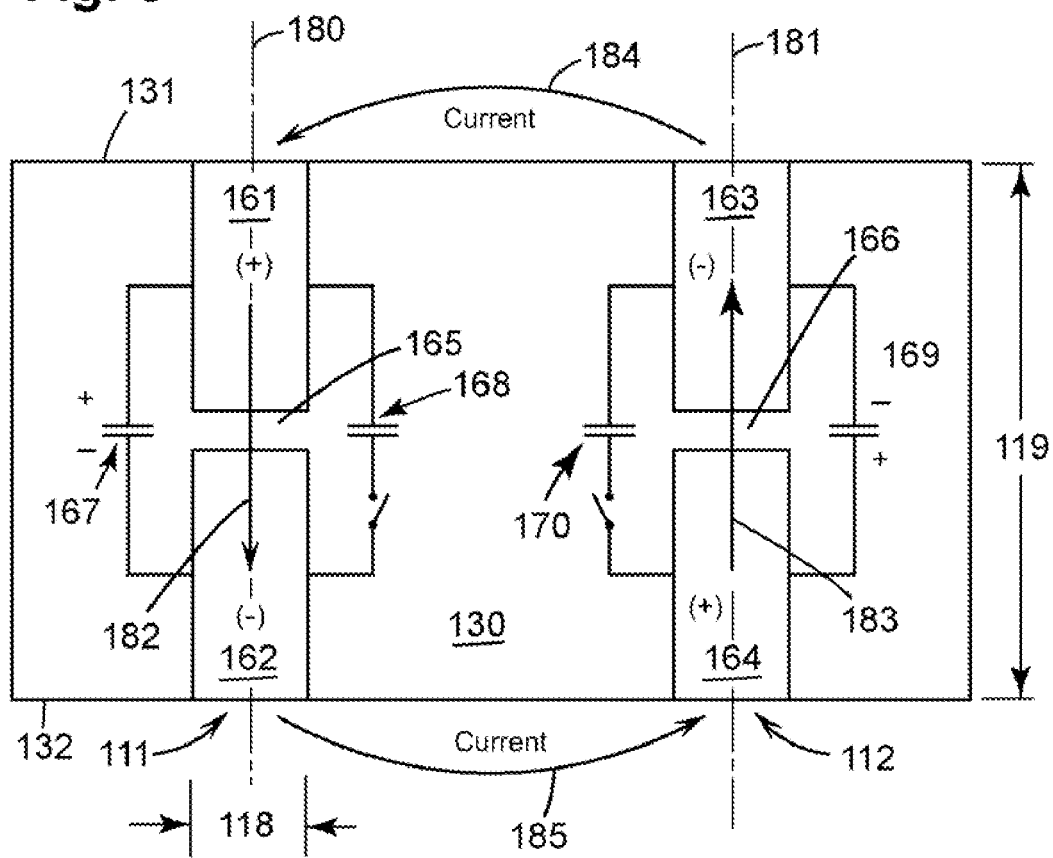
FIG. 3 is a diagram illustrating current flow in an embodiment of an inductive sensor that forms part of the asymmetric shoe scanner of FIG. 1.

FIG. 3 is a simplified schematic diagram depicting some of the primary electrical components of the inductive sensor 110. Illustratively, the conductive trace 111 is shown having fore conductive element 161 and aft conductive element 162, which are separated by a non-conductive gap 165. Similarly, the conductive trace 112 includes fore conductive element 163 and aft conductive element 164, which are also separated by a non-conductive gap 166. The conductive traces 111,112 may be formed from any suitably electrically conductive material. Non-limiting examples of suitable electrically conductive materials include such as copper or aluminum, for example.

The length and width of the conductive traces 111,112 will vary for each embodiment of the invention. In an exemplary embodiment, each conductive trace 111, 112 may each have a width 118 of about 10.2 cm to about 20.3 cm and a length 119 (including the gap 165,166) of about 30.5 cm to about 61 cm. Each gap 165,166 may be about 0.3 cm to about 2.5 cm across, as measured from the aft edges of the conductive elements 161,163 to the fore edges of the corresponding conductive elements 162,164.

Conductive element 161 and the conductive element 162 of the conductive trace 111 are shown electrically coupled by fixed-valued resonance capacitor 167 and tuning capacitor 168, which may be a switched capacitor having a variable capacitance. Additionally, the conductive element 163 and the conductive element 164 of the conductive trace 112 are shown similarly electrically coupled by fixed-value resonance capacitor 169 and tuning capacitor 170.

FIG. 3 also includes several arrows 182, 183, 184, 185 which show the direction of current flow through the conductive traces 111,112 in a current loop associated with an embodiment of the invention. A skilled artisan will appreciate that current may flow in one of several current loops depending on how the shoe scanner is operated. In the current loop represented by arrows 182, 183, 184, and 185, the current flows through the conductive trace 111 in one direction as indicated by the arrow 182 (e.g., from a positively charged fore conductive element 161 to a negatively charged aft conductive element 162), and also flows through the conductive trace 112 in the opposite direction as indicated by the arrow 183 (e.g., from a positively charged aft conductive element 164 to a negatively charged fore conductive element 163). In this current loop, the conductive traces 111,112 are said to have "asymmetric current flows" 182,183.

Since the fore edge 131 of the printed circuit board 130 is electrically coupled with the recessed housing 150, current also flows in the direction indicated by arrow 184 (e.g., from the negatively charged fore conductive element 163 of the conductive trace 112 to the positively charged aft conductive element 161 of the conductive trace 111). Since the aft edge 132 of the printed circuit board 130 is electrically coupled with the recessed housing 150, current also flows in the direction of arrow 185 (e.g., from the negatively charged aft conductive element 162 of the conductive trace 111 to the positively charged aft conductive element 164 of the conductive trace 112).

Referring to FIGS. 2 and 3, each conductive trace 111,112 may include two sets of conductive elements and two sets of relays and capacitors, which are geometrically configured and positioned to minimize electromagnetic interference. Illustratively, the conductive trace 111 includes conductive elements 161,162, which are separated by a gap 165. Likewise, the conductive trace 112 includes conductive elements 163,164, which are separated by a gap 166. The conductive trace 111 includes a first set of relays and capacitors 171 and a corresponding second set of relays and capacitors 172. Within each set 171,172, the relays and capacitors are arranged in one or more strips. These strips are electrically insulated from each other and substantially parallel the longitudinal axis 180. A majority of the set of relays and capacitors 171 may be positioned on the aft end of the conductive element 161 on a first side of the conductive trace's longitudinal axis 180. To balance and effectively cancel any electromagnetic interference emitted by the relays and capacitors, the second set of relays and capacitors may be positioned on the second side of the conductive trace's center vertical axis 180. Additionally, the second set of relays and capacitors 172 may be rotated by 180 degrees from the orientation of the first set of relays and capacitors 171. A majority of the second set of relays and capacitors 172 may also be positioned on the fore end of the conductive element 162.

Referring to the second conductive trace 112, the third and fourth sets of relays and capacitors 173,174 may be configured in the manner described above, and may be further configured to mirror the symmetry of the first and second sets of relays and capacitors 171,172. For example, as shown in FIG. 2, a majority of the third set of relays and capacitors 173 may be positioned on the aft end of the conductive element 163 on a first side of the conductive trace's longitudinal axis 181. The fourth set of relays and capacitors 174 may be positioned on a second side of the conductive trace's longitudinal axis 181 and rotated by 180 degrees from the orientation of the third set of relays and capacitors 173. A majority of the fourth set of relays and capacitors 174 may be positioned on the fore end of the conductive element 164.

Figure 4:
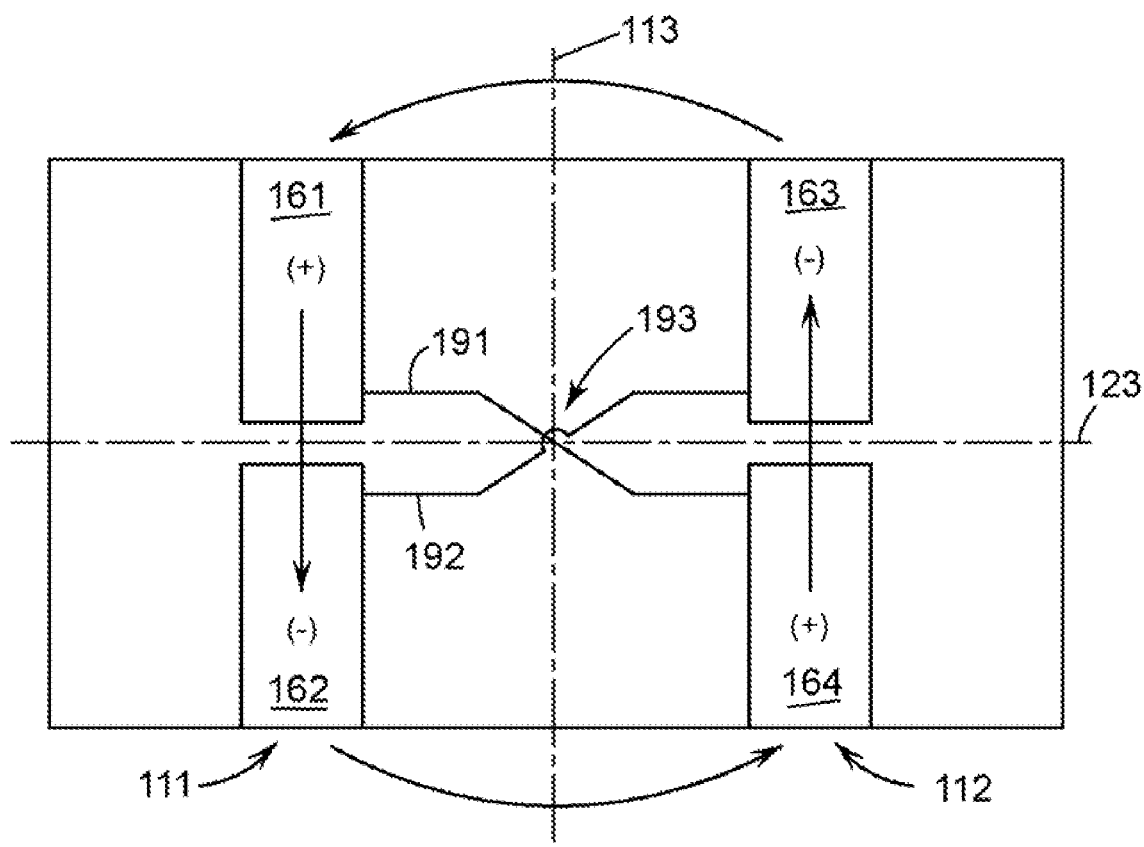
FIG. 4 is a diagram that illustrates placement of a pair crossed, electrically conductive, balancing wires according to an embodiment of the invention.

FIG. 4 is a simplified schematic diagram depicting optional current balance wires 191,192 in communication with the conductive traces 111,112 of the inductive NQR sensor 110. Note that FIG. 4 depicts the same embodiment of the inductive NQR sensor 110 of FIG. 3, but fixed-valued resonance capacitors 167,169 and tuning capacitors 168,170 of the conductive traces 111,112 have been omitted for clarity.

In FIG. 4, current balance wire 191 is shown electrically coupling positively charged fore conductive element 161 and positively charged aft conductive element 164. A second current balance wire 192, which crosses the current balance wire 192 at intersection 193, similarly couples negatively charged aft conductive element 162 and negatively charged fore conductive element 163. Additionally, the current balance wires 191,192 should be electrically insulated from each other. The balance wires 191,192 assist the NQR sensor 110 in maintaining the above-described anti-symmetric flow of current 182,183 through the conductive traces 111,112. In addition, the balance wires 191,192 maintain the positive and negative conductive elements of the conductive traces 111,112 at about the same current level.

In an embodiment where the balancing shim 140 described above is used, the balance wires 191,192 (and their intersection 193) may be positioned at about the intersection of the medial plane 113 and the lateral center axis 123, as shown. Alternatively, in an embodiment where the balancing shim 140 is not used, the balance wires 191,192 (and their intersection 193) may be moved aft of the lateral center axis 123 to reflect a magnetic field generated by an inductive NQR sensor 110,120 forward toward the end wall 104, as further described below with reference to FIG. 8.

Figure 5:
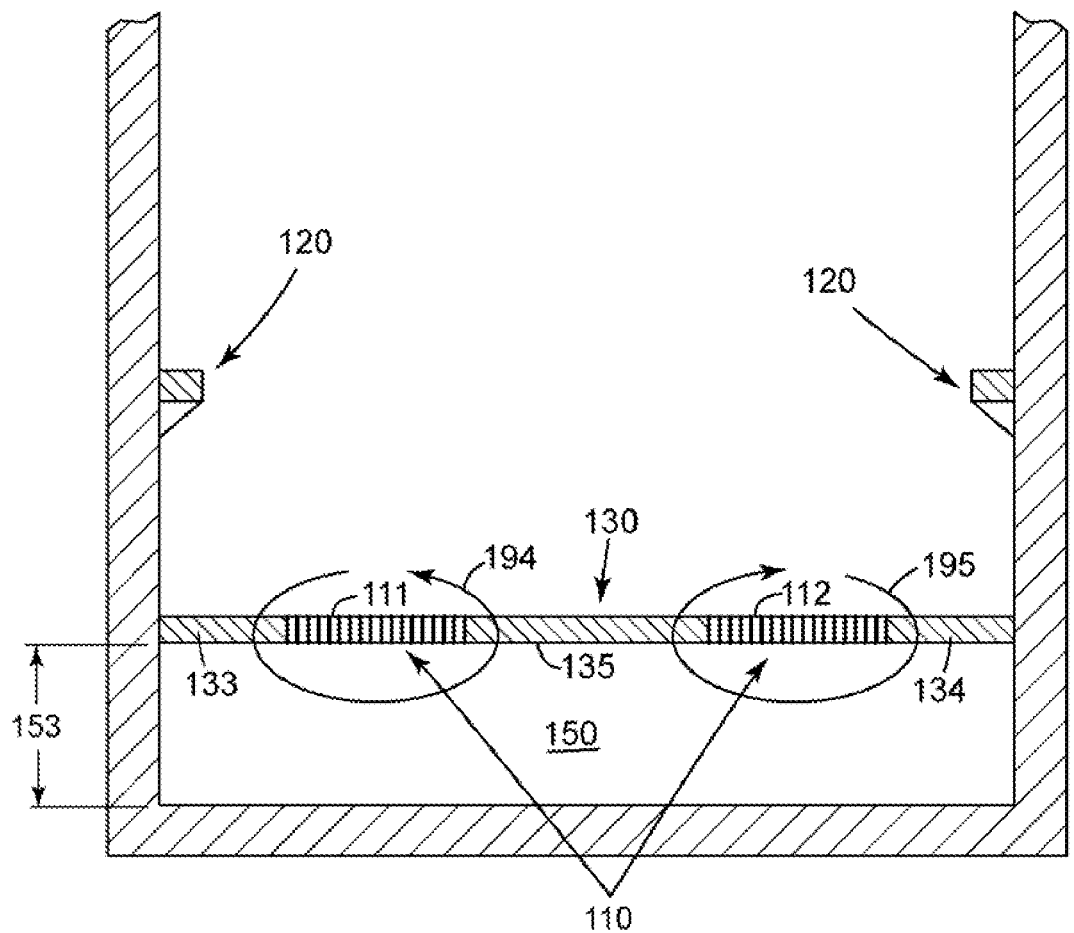
FIG. 5 is a cross-sectional view of the asymmetric shoe scanner of FIG. 1 taken along the line B-B'.

FIG. 5 is a partial cross-sectional view of the security inspection system 10, taken along the sectional lines B-B' in FIG. 1, showing an embodiment of an inductive NQR sensor 110 positioned within the passive electromagnetic shield described above (e.g., within an interior region of the side walls 102,103 and end wall 104). Arrow 194 indicates the counter-clockwise circulation direction of the magnetic field produced by current flowing in the conductive trace 111. Arrow 195 indicates the clockwise circulation direction of the magnetic field produced by the current flowing in the conductive trace 112. In contrast to conventional inductive sensor systems, the asymmetric magnetic fields (represented by arrows 194,195) generated by the inductive NQR sensor 110 are well-attenuated, self-contained, and are especially suited for use with open-access shielding structures. For example, the resulting pattern of the magnetic fields (represented by arrows 194,195) generated by inductive NQR sensor 110 experiences an approximately exponential drop in strength along a radial direction given by the following formula:

$$e = r/w \qquad (1)$$

where 'r' is the radius of the walls (distance 196 of FIG. 1) and 'w' is the lateral spacing between the walls (distance "W" of FIG. 1).

In an embodiment, the inductive sensor 110 may be coupled with the recessed housing 150 to form a non-conductive gap 153 between the circuit board 130 containing the conductive traces 111,112 of the inductive sensor 110 and a bottom 154 of the recessed housing 150. This gap 153 allows the magnetic fields 194,195 to freely circulate about their respective conductive traces 111,112. In an embodiment, a minimum depth of the gap 153 would be about 5.1 cm.

As mentioned above, the inductive sensor 110 may be implemented using a printed circuit board 130, which electrically insulates the conductive traces 111,112 from each other, and from conductive walls 102,103 via regions 133, 134,135 of the printed circuit board 130 that are non-electrically conductive. These non-conductive regions of the printed circuit board 130 also permit the magnetic fields 194,195 to freely circulate about their respective conductive traces. As an example of a practical application, the conductive traces 111, 112 may be positioned about 5.1 cm to about 17.8 cm from their respective walls 102,103 by the lateral non-conductive regions 133 and 134 of the printed circuit board 130, respectively. In addition, the conductive traces may be positioned about 10.2 cm to about 35.6 cm from each other using the center non-conductive region 135 of the printed circuit board 130.

In FIG. 5, the conductive traces 111,112 are shown having approximately the same thickness as the printed circuit board 130, but this is not a requirement; and in some embodiments, the conductive traces 111, 112 may be thinner than the thickness of the printed circuit board 130. A non-limiting example of a range of thickness for each of the conductive traces 111,112 is about 0.2 cm to about 1.6 cm, but other thicknesses are possible.

Figure 6:
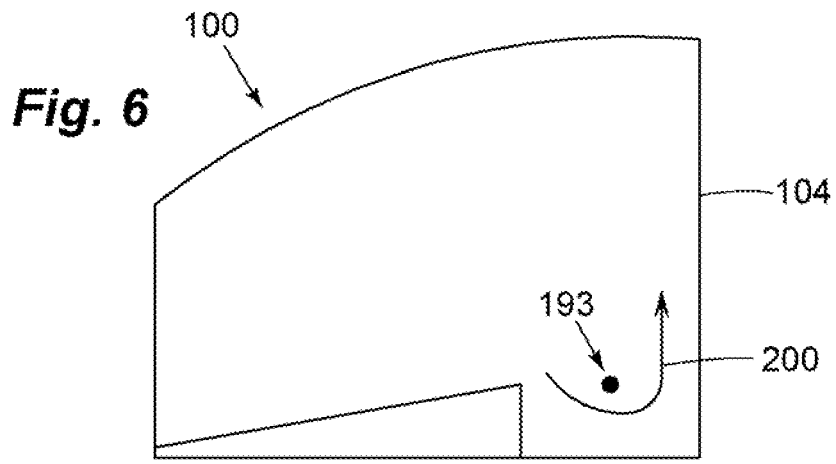
FIG. 6 is a right-hand, side view of the asymmetric shoe scanner of FIG. 1 showing an unbalanced magnetic field.
Figure 7:
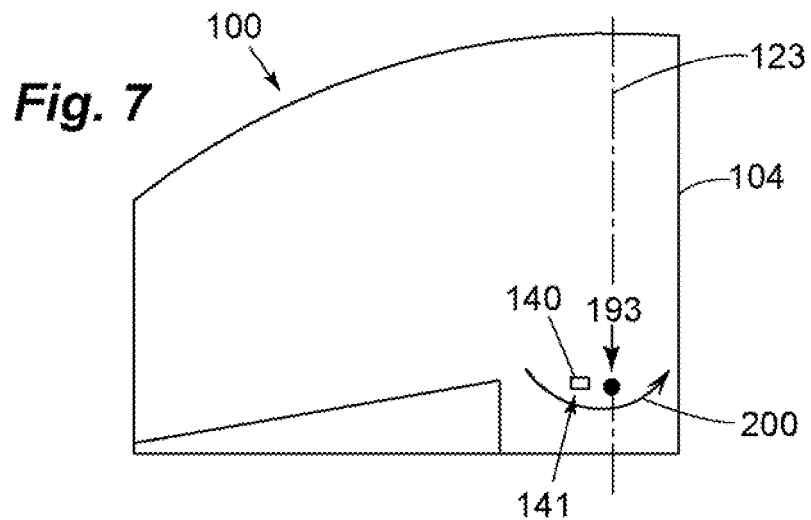
FIG. 7 is a right-hand, side view of the asymmetric shoe scanner of FIG. 1 illustrating how placement of an electrically conductive shim can effectively balance the unbalanced magnetic field shown in FIG. 6.
Figure 8:
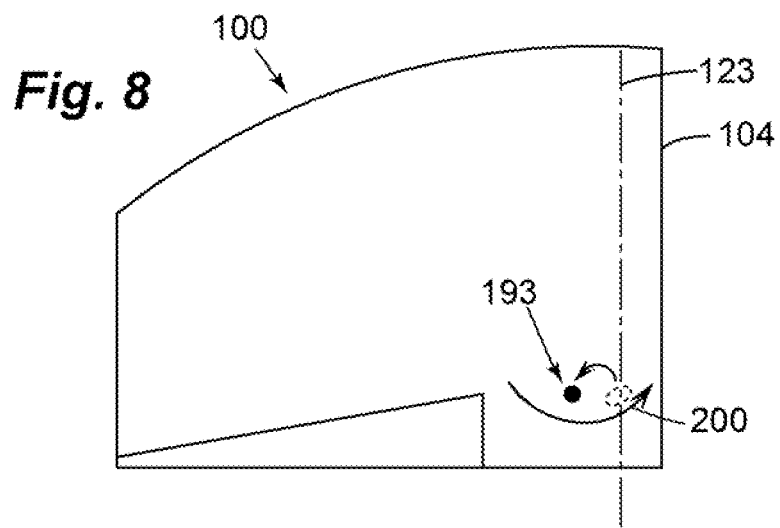
FIG. 8 is a right-hand, side view of the asymmetric shoe scanner of FIG. 1 that illustrates how placement of crossed, electrically conductive wires can effectively balance the unbalanced magnetic field shown in FIG. 6.

FIGS. 6, 7, and 8 are simplified cross-sectional side views of the asymmetric shoe scanner 100 of FIGS. 1 and 2. FIG. 6 illustrates a problem for which embodiments of the invention provide a technical solution. FIGS. 7 and 8 illustrate embodiments of the invention that solve the problem shown in FIG. 6.

Referring to FIG. 6, a counter-clockwise circulating magnetic field 200 is generated by the current flowing through the intersection 193 of the crossed balancing wires 191,192. This magnetic field 200 is reflected sharply upwards away from the floor 101 and/or the bottom of the recessed housing 150 by the end wall 104. Consequently, the magnetic field 200 becomes unbalanced in the fore/aft directions, which impairs operation of the asymmetric shoe scanner 100.

Referring to FIGS. 2 and 7, the magnetic field 200 may be balanced (e.g., reflected toward the end wall 104) by placement of the balancing shim 140 as previously described. Since the balancing shim 140 is electrically conductive, it repels the magnetic field 200. Placement of the balancing shim's fore edge 141 at or aft of the lateral center axis 123 alters the shape of the magnetic field 200 so that it is more evenly distributed fore and aft of the lateral center axis 123. This significantly improves operation of the asymmetric shoe scanner 100.

Referring to FIGS. 4 and 8, another way of balancing the magnetic field 200 is to shift the crossed balancing wires 191,192 (including their intersection 193) aft of the lateral center axis 123. When the crossed balancing wires 191,192 are positioned as shown in FIG. 8, the magnetic field 200 is not reflected upward by the end wall 104 as sharply as shown in FIG. 6. Accordingly, the shifted placement of the crossed balancing wires 191,192 alters the shape of the magnetic field 200 so that the magnetic field 200 is more evenly distributed fore and aft of the lateral center axis 123.

Figure 9:
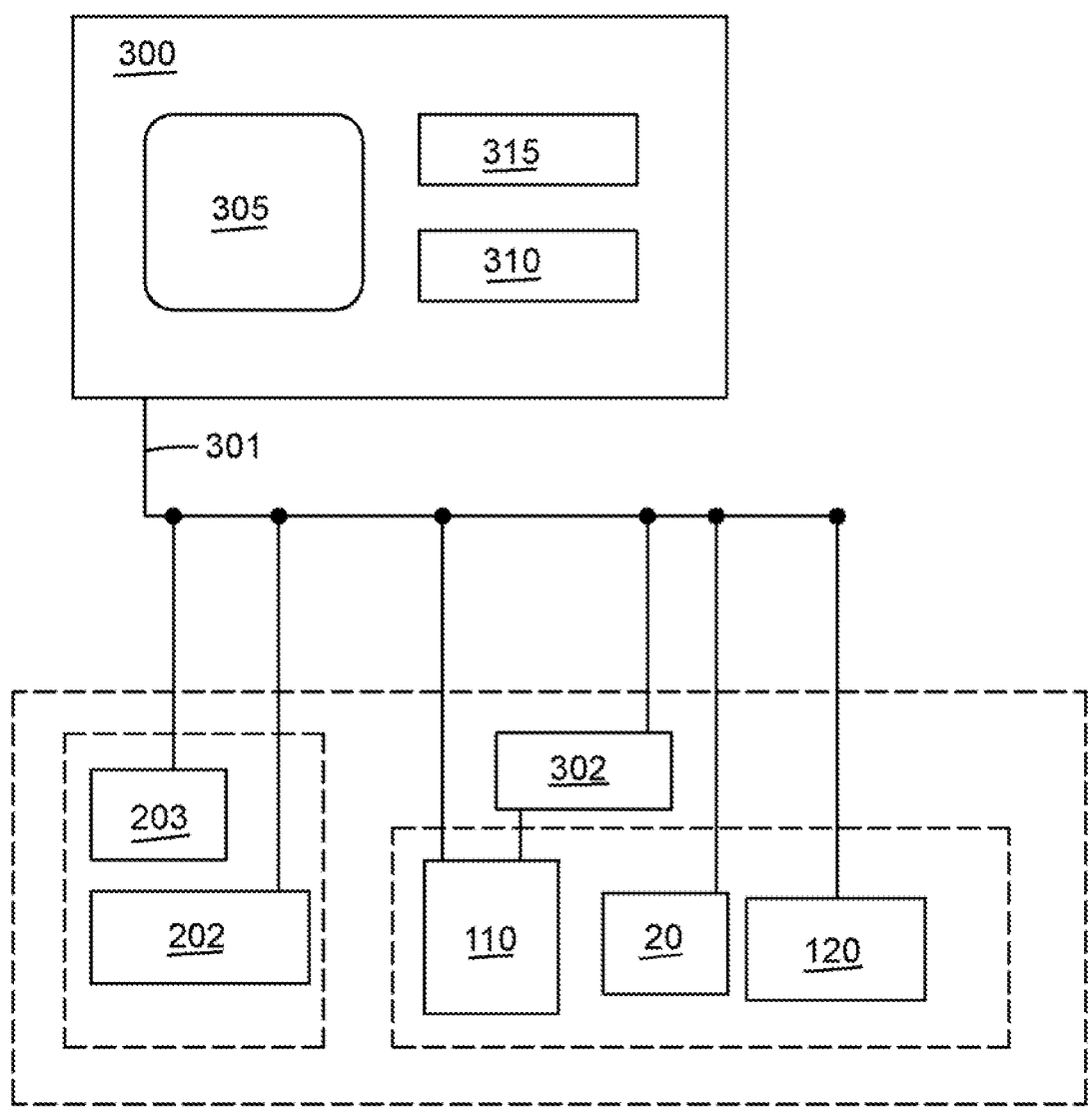
FIG. 9 is a schematic diagram of a computer control system that may be used to operate embodiments of the asymmetric shoe scanner of FIG. 1.

FIG. 9 is a diagram illustrating an embodiment of a computer system 300 that may be used to operate one or more components of the inspection system 10. The computer system 300 is illustratively shown having a graphical user interface 305, processor 310, and memory 315. The processor 310 may be implemented using any suitable computational device that provides the necessary control, monitoring, and data analysis of the various systems and components associated with the inspection system 10, including electrical source 302.

In general, processor 310 may be a specific or general purpose computer such as a personal computer having an operating system such as DOS, Windows, OS/2 or Linux; Macintosh computers; computers having JAVA OS as the operating system; graphical workstations such as the computers of Sun Microsystems and Silicon Graphics, and other computers having some version of the UNIX operating system such as AIX or SOLARIS of Sun Microsystems; or any other known and available operating system, or any device including, but not limited to, laptops and hand-held computers. Graphical user interface 305 may be any suitable display device operable with any of the computing devices described herein and may comprise a display such as an liquid crystal display, light emitting diode display, cathode ray tube display, plasma display, and the like.

The communication link 301 between system 300 and the various inspection and detector systems may be implemented using any suitable technique that supports the transfer of data and necessary signaling for operational control of the various components of the inspection system 10 (for example, inductive NQR sensor 110, metal detector sensor 120, and kiosk 20, trace detection portal 202, air jets 203, among others). The communication link 301 may be implemented using conventional communication technologies such as unshielded twisted pair (UTP) cables, Ethernet cables, coaxial cables, serial cables, parallel cables, and optical fibers, among others. Although the use of wireless communication technologies is possible, they are typically not utilized since they may not provide the necessary level of security required by many applications such as airport baggage screening systems.

In some implementations, system 300 is physically configured in close physical proximity to the inspection system, but system 300 may be remotely implemented if so desired. Remote implementations may be accomplished by configuring system 300 and the inspection system with a suitably secure network link that comprises anything from a dedicated connection, to a local area network (LAN), to a wide area network (WAN), to a metropolitan area network (MAN), or even to the Internet.

Exemplary methods of using and/or operating an embodiment of the inspection system 10 are now described. Referring to FIGS. 1 and 2, a person may enter the inspection system 10 at the open end 13 of the channel 106 and proceed to the identification kiosk 20. While interacting with the identification kiosk 20, the person may stand with their feet positioned over (or adjacent to) the conductive traces 111,112 of the NQR sensor 110 and adjacent to the metal detector conductive traces 121,122 of the metal detection sensor 120. Through the use of sensing means (e.g., visual inspection, infrared laser, pressure sensor, heat sensor, touch pad, camera, etc.) the inspection system 10 may detect the presence of a person or an item within the scanning area 107, and then excite the conductive traces 111,112, 121,122 with electromagnetic signals at a pre-determined resonance frequency corresponding to a predetermined, characteristic NQR/NMR frequency of an pre-determined alarm object. For example, RDX-based plastic explosives have a resonant frequency of approximately 3.410 MHz, while PETN-based plastic explosives have a resonant frequency of approximately 890 KHz. Note that the excitation frequency need not be exactly the same as the target substance NQR frequency, but it is typically within a range of plus or minus about 500 Hz to about 1000 Hz. The resonant frequencies of the various target substances of interest that may be detected using NQR are well known and need not be further described.

The RF excitation signals create self-contained, balanced, magnetic fields 194,195,200 around the lower extremities of the inspected person that are within (or about an item placed in) the scanning area 107. After transmitting the RF excitation signals, the conductive traces 111,112 act as pickup coils that detect any resonance signals received from the substance of interest. These reflected resonance signals may be communicated to the computer system 300 for processing and analysis. After analysis is complete, the computer system 300 may output an indication of whether an alarm object, substance of interest, etc. is present within the scanning area of the shoe scanner 100. In an embodiment, the NQR scanning process requires about 2 seconds to about 20 seconds, which provides for quick, accurate, non-intrusive inspection of the lower extremities of an inspected person.

Figure 10:
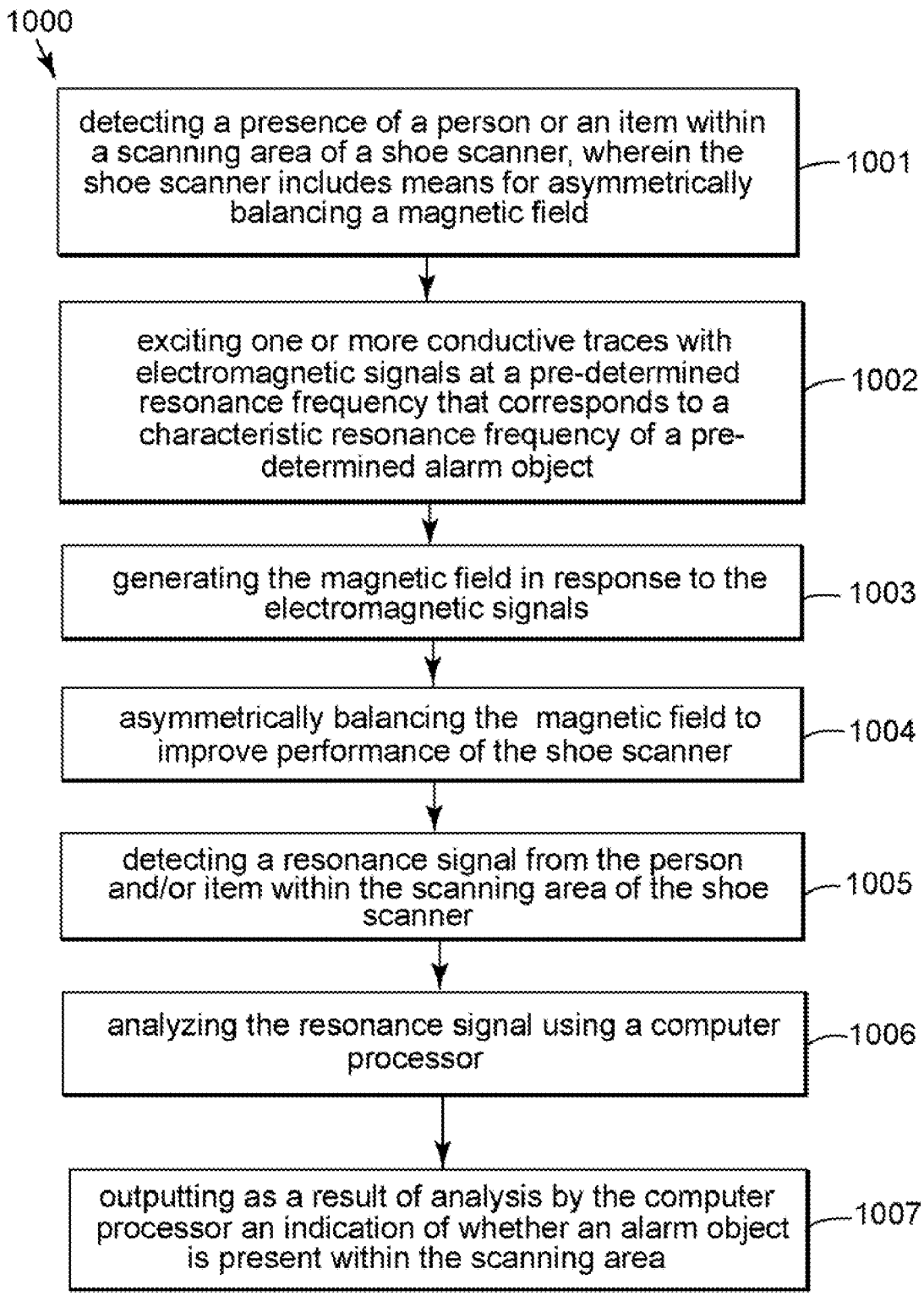
FIG. 10 is a flowchart of a method according to an embodiment of the invention.

FIG. 10 is a flowchart of a method 1000 according to an embodiment of the invention. The method 1000 comprises an optional step 1001 of detecting a presence of a person or an item within a scanning area of a shoe scanner, wherein the shoe scanner includes means for asymmetrically balancing a magnetic field. This may be accomplished visually by a person operating an embodiment of the invention, and/or via known detection means, such as laser beams, video cameras, pressure sensors, etc. The method may further include the step 1002 of exciting one or more conductive traces with electromagnetic signals at a pre-determined resonance frequency that corresponds to a characteristic resonance frequency of a pre-determined alarm object. The method may further include a step 1003 of generating the magnetic field in response to the electromagnetic signals, and the step 1004 of asymmetrically balancing the magnetic field to improve performance of the shoe scanner. The method may yet further include the step 1005 of detecting a resonance signal from the person and/or item within the scanning area of the shoe scanner. The method may also include the step 1006 of analyzing the resonance signal using a computer processor. The method may further include the step 1007 of outputting, as a result of analysis by the computer processor, an indication of whether an alarm object is present.

Additionally or alternatively, an RF excitation signal at a pre-determined resonant frequency may be used to detect a metallic shoe shank in shoes worn by an inspected person. As previously described, the energized metal detector conductive traces 121,122 generate a uniform magnetic field if no metal object is present in the scanning area. If a shoe shank, however, is present within the scanning area, the metal that forms the shoe shank will disrupt the balanced magnetic field 194,195, and 200. This disruption may be detected by the conductive traces 111,112 and analyzed by the computer system 300 to confirm that a metallic shoe shank is present in the scanning area.

Figure 11:
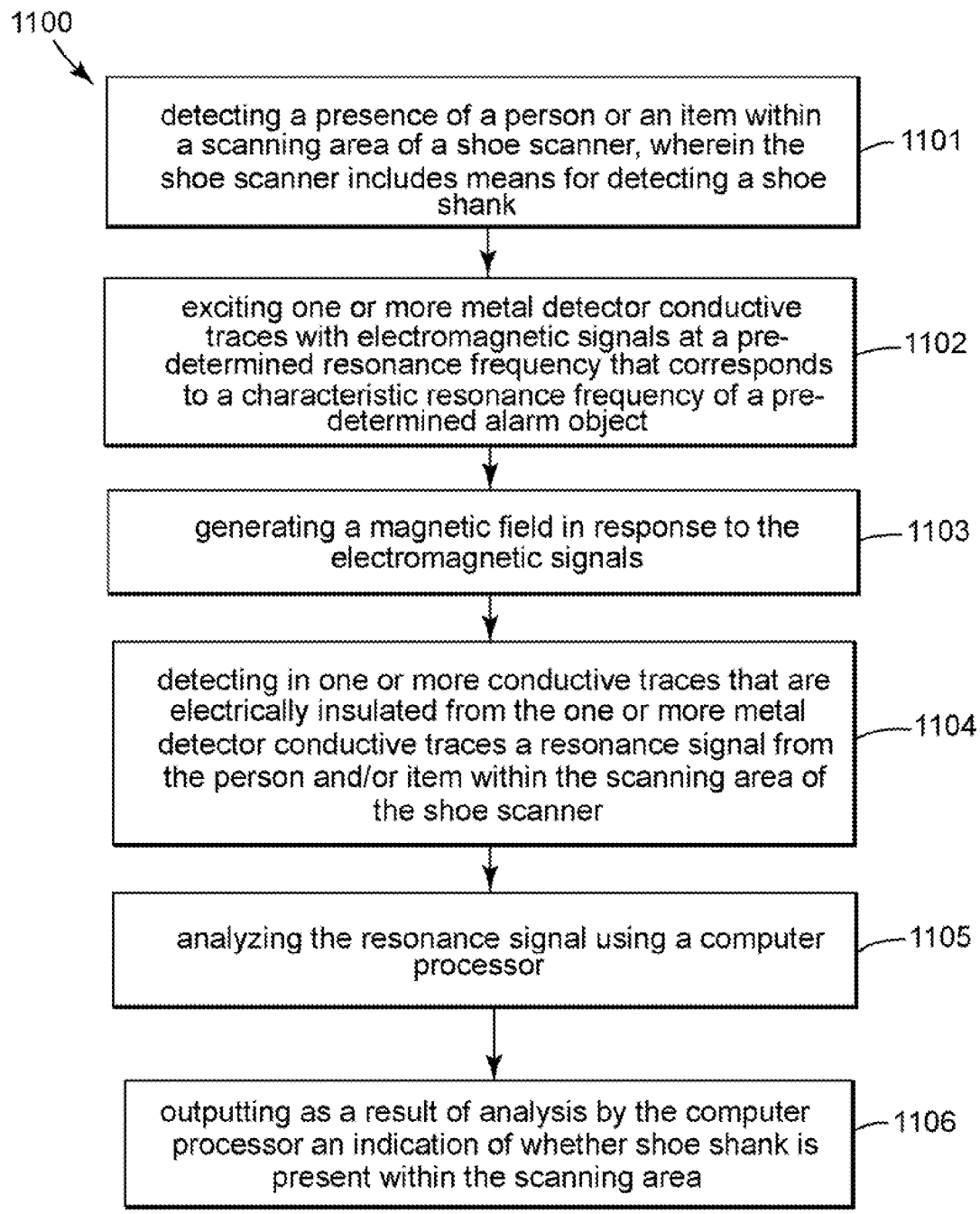
FIG. 11 is a flowchart of another method according to an embodiment of the invention.

FIG. 11 is a flowchart 1100 of a method according to an embodiment of the invention. The method 1100 comprises an optional step 1101 of detecting a presence of a person or an item within a scanning area of a shoe scanner, which includes means for detecting a shoe shank. This may be accomplished visually by an operator of an embodiment of the invention and/or via known detection means, such as laser beams, video cameras, pressure sensors, etc. The method may further include the step 1102 of exciting one or more metal detector conductive traces with electromagnetic signals at a pre-determined resonance frequency that corresponds to a characteristic resonance frequency of a pre-determined alarm object. The method may further include the step 1103 of generating a magnetic field in response to the electromagnetic signals. The method may further include the step 1104 of detecting in one or more conductive traces that are electrically insulated from the one or more metal detector conductive traces a resonance signal from the person and/or item within the scanning area of the shoe scanner. The method may also include the step 1105 of analyzing the resonance signal using a computer processor. The method may yet further include the step 1106 of outputting, as a result of analysis by the computer processor, an indication of whether the shoe shank is present, may also be included in the method. It is understood that these method steps may be performed in any suitable order.

Note that footwear, socks, and other clothing items need not be removed prior to inspection. These items can be inspected by the inspection system 10 while being worn by the inspected person. Since the inspected person is not required to remove such items before inspection, the inspection system 10 is especially suited for the non-intrusive inspection of passengers as part of a multi-station, airport screening checkpoint.

Figure 12:
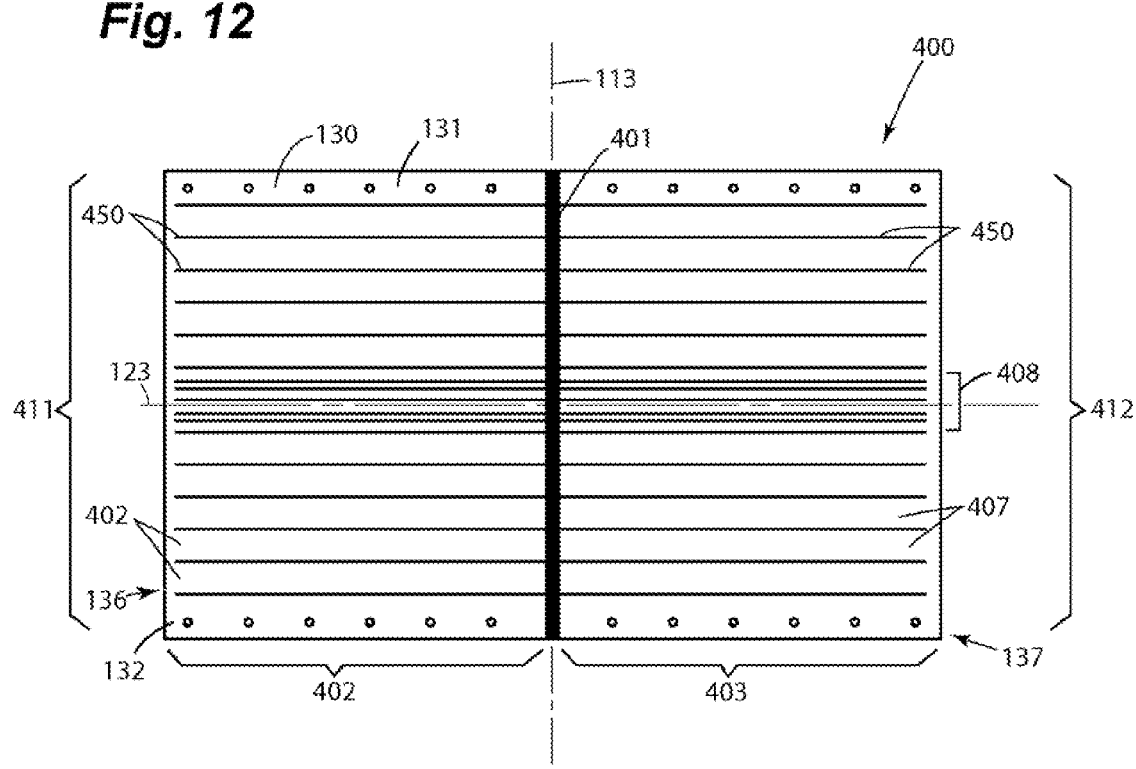
FIG. 12 is a diagram illustrating an embodiment of a shielding device that may be used to protect the NQR/NMR magnetic fields in an inspection scanner from electronic interference.

FIG. 12 is a diagram illustrating an embodiment of a shielding device 400 that may be used to protect the inductive NQR sensor 110, 120 from electronic interference. The shielding device 400 may be integrated within or on an exterior surface of the printed circuit board 130. As shown in FIG. 12, the printed circuit board 130 has a medial plane 113, which intersects an orthogonal lateral center axis 123. Parts of the shielding device 400 include an electrically conductive main trace 401 and one or more sets of electrically conductive secondary traces 402,403 that are electrically coupled with the main trace 401. The main trace 401 may be centered and evenly distributed on either side of the medial plane 113 and/or on either side of the lateral center axis 123. A length 405 of the main trace 401 may be measured from at or proximate the fore edge 131 of the printed circuit board 130 to at or proximate the aft edge of the printed circuit board 130. The length 405 of the main trace 401 may be greater than its width 406. In an embodiment, the width 406 of the main trace may be greater than a width of any one of the secondary traces in the sets of secondary traces 402,403.

In FIG. 12, the set of secondary traces 402 is positioned on one side of the medial plane 113, and the set of secondary traces 403 is positioned on the opposite side of the medial plane. Each trace 450 in the sets of secondary traces 402,403 is electrically connected with the main trace 401. Additionally, each trace is positioned orthogonally, or substantially orthogonally, to the main trace 401, and insulative gaps 407 separate each of the secondary traces. In an embodiment, a center region 408 of the shielding device 400 has a higher density of secondary traces than a fore region 409 and/or an aft region 410 of the shielding device 400. As used herein, the phrase "higher density of secondary traces" means that the secondary traces are closely spaced together, or equivalently, that the gaps 407 between the secondary traces are small. As shown, the ends 411 of the traces 450 of the set of secondary traces 402 may end at or proximate the lateral edge 136 of the printed circuit board 130. In like manner, the ends 412 of the traces 450 of the set of secondary traces 403 may end at or proximate the lateral edge 137 of the printed circuit board 130. In an embodiment, the ends 411 are spaced apart from each other and do not electrically connect with a side trace. In like manner, the ends 412 are also spaced apart from each other and do not electrically terminate in a side trace.

In an alternative embodiment, the ends 411 of the traces 450 of the set of secondary traces 402 may electrically connect with a first side trace that parallels (or substantially parallels) the main trace 401, and the ends 412 of the traces 450 of the set of secondary traces 403 may electrically connect with a second side trace that parallels (or substantially parallels) the main trace 401. In use, the shielding device 400 absorbs the electric field associated with the capacitors 167, 168,169, 170, leaving all or most of the magnetic field generated by the inductive NQR sensor 110,120 intact. This significantly enhances operation of the inspection system 10.

One or more steps of the methods and processes described herein may be implemented in a computer-readable medium using, for example, computer software, hardware, or some combination thereof. For a hardware implementation, the embodiments described herein may performed by processor 310, which may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a selective combination thereof.

For a software implementation, the embodiments described herein may be implemented with separate software modules, such as procedures, functions, and the like, each of which perform one or more of the functions and operations described herein. The software codes can be implemented with a software application written in any suitable programming language and may be stored in a memory unit (for example, memory 315), and executed by a processor (for example, processor 310). The memory unit may be implemented within the processor or external to the processor, in which case it can be communicatively coupled to the processor using known communication techniques. An exemplary memory unit 315 may be implemented using any type (or combination) of suitable volatile and non-volatile memory or storage devices including random access memory (RAM), static random access memory (SRAM), electrically erasable programmable read-only memory (EEPROM), erasable programmable read-only memory (EPROM), programmable read-only memory (PROM), read-only memory (ROM), magnetic memory, flash memory, magnetic or optical disk, or other similar or effective memory or data storage device.

A detailed description of various embodiments of the invention has been provided; however, modifications within the scope of the invention will be apparent to persons having ordinary skill in the above-referenced technological field. Such persons will appreciate that features described with respect to one embodiment may be applied to other embodiments. Thus, the scope of the invention is to be properly construed with reference to the following claims.

What is claimed is:

1. An inspection system, comprising:
    an electromagnetic shield having a medial plane and a scanning area;
    an inductive sensor configured to inspect a portion of a lower extremity of a person for a presence of an item of interest, wherein the inductive sensor comprises electrically conductive traces positioned on opposing sides of the medial plane; and
    a magnetic field balancing apparatus positioned between, and electrically insulated from, the electrically conductive traces.

2. The inspection system of claim 1, wherein the item of interest is one of an explosive, a weapon, a drug and a combination thereof.

3. The inspection of claim 1, further comprising:
    a radio frequency (RF) subsystem having a variable frequency RF source in communication with the inductive sensor and configured to provide an RF excitation signal at a frequency generally corresponding to a predetermined, characteristic nuclear quadrupolar resonance (NQR) frequency of the item of interest,
    wherein the inductive sensor is configured to function as a pickup coil for NQR signals generated in response to the RF excitation signal, and further configured to provide a NQR output signal indicative of a presence or absence of the item of interest.

4. The inspection system of claim 1, wherein the inductive sensor is one of a nuclear quadrupole resonance (NQR) sensor and a nuclear magnetic resonance (NMR) sensor.

5. The inspection system of claim 1, further comprising:
a kiosk configured to verify an identity of the person.

6. The inspection system of claim 1, wherein the magnetic field balancing apparatus comprises an electrically conductive shim.

7. The inspection system of claim 6, wherein an edge of the electrically conductive shim is positioned at or below a lateral center axis of the electromagnetic shield.

8. The inspection system of claim 1,
wherein each of the electrically conductive traces comprises a fore conductive element that is separated from an aft conductive element by a non-electrically conductive gap, and
wherein the magnetic field balancing apparatus comprises a pair of balance wires that connect the electrically conductive traces and which are crossed.

9. The inspection system of claim 8, wherein a position at which the pair of balance wires cross is located at or below a lateral center axis of the electromagnetic shield.

10. The inspection system of claim 8, wherein the pair of balance wires comprises:
a first balance wire electrically coupled with the fore conductive element of a first conductive trace of the electrically conductive traces to the aft conductive element of a second conductive trace of the electrically conductive traces; and
a second balance wire crossed with the first balance wire and electrically coupled with the aft conductive element of the first conductive trace and the fore conductive element of the second conductive trace.

11. The inspection system of claim 8, further comprising:
a first set of switches and relays formed in the fore conductive element on a first side of a longitudinal axis of the fore and aft conductive elements; and
a second set of switches and relays formed in the aft conductive element on a second side of the longitudinal axis of the fore and aft conductive elements,
wherein a geometry of the first set of switches and relays differs by 180 degrees from a geometry of the second set of switches and relays.

12. The inspection system of claim 1, wherein the electromagnetic shield comprises:
three walls positioned to define the scanning area;
a substrate coupled orthogonally with each of the three walls and having a recessed housing therein, wherein the substrate, the recessed housing and the three walls each comprise an electrically conductive material.

13. The inspection system of claim 12, wherein one wall of the three walls comprises part of a kiosk.

14. The inspection system of claim 12, further comprising:
a metal detection sensor that is electrically insulated from the inductive sensor.

15. The inspection system of claim 14, wherein the metal detection sensor comprises:
a first metal detector conductive trace positioned above the substrate; and
a second metal detector conductive trace positioned above the substrate and opposite the first metal detector conductive trace.

16. The inspection system of claim 1, further comprising:
a symmetrically balanced geometrical arrangement of relays and capacitors used to operate the inductive sensor.

17. An inspection system, comprising:
an electromagnetic shield having a medial plane and a scanning area;
an inductive sensor configured to inspect a portion of a lower extremity of a person for a presence of an item of interest, wherein the inductive sensor comprises electrically conductive traces positioned on opposing sides of the medial plane; and
a shielding device configured to protect a magnetic field associated with the electrically conductive traces from external electromagnetic interference.

18. The inspection system of claim 17, further comprising:
a printed circuit board symmetrically positioned about the medial plane and having the inductive sensor and the shielding device formed on opposing sides thereof.

19. The inspection system of claim 18, wherein the shielding device comprises:
an electrically conductive main trace disposed along the medial plane; and
one or more sets of electrically conductive secondary traces that are electrically coupled with the main trace.

* * * * *